US 8,374,671 B2

(12) United States Patent
Barnes

(10) Patent No.: US 8,374,671 B2
(45) Date of Patent: Feb. 12, 2013

(54) HEALTH INDICATOR

(75) Inventor: Richard Barnes, Suckley (GB)

(73) Assignee: Select Research Limited, Birmingham (GB)

( * ) Notice: Subject to any disclaimer, the term of this patent is extended or adjusted under 35 U.S.C. 154(b) by 760 days.

(21) Appl. No.: 12/280,985

(22) PCT Filed: Feb. 27, 2007

(86) PCT No.: PCT/GB2007/000660
§ 371 (c)(1),
(2), (4) Date: Dec. 22, 2008

(87) PCT Pub. No.: WO2007/096652
PCT Pub. Date: Aug. 30, 2007

(65) Prior Publication Data
US 2009/0099457 A1   Apr. 16, 2009

Related U.S. Application Data

(60) Provisional application No. 60/782,147, filed on Mar. 14, 2006.

(30) Foreign Application Priority Data

Feb. 27, 2006   (GB) .................................. 0603864.0

(51) Int. Cl.
*G01B 11/22* (2006.01)
(52) U.S. Cl. ...................................... 600/407; 356/627
(58) Field of Classification Search .................. 600/301, 600/411, 416, 459, 340; 356/627, 601, 628; 128/921
See application file for complete search history.

(56) References Cited

U.S. PATENT DOCUMENTS

| 4,825,263 | A | 4/1989 | Desjardins et al. | |
|---|---|---|---|---|
| 2001/0030754 | A1* | 10/2001 | Spina et al. | 356/601 |
| 2002/0026105 | A1* | 2/2002 | Drazen | 600/300 |
| 2003/0120515 | A1* | 6/2003 | Geller | 705/2 |
| 2004/0143194 | A1* | 7/2004 | Kihara et al. | 600/534 |
| 2004/0186395 | A1 | 9/2004 | Vastano | |
| 2005/0014113 | A1* | 1/2005 | Fleck et al. | 434/247 |
| 2006/0129436 | A1* | 6/2006 | Short | 705/4 |

FOREIGN PATENT DOCUMENTS

| EP | 1374767 A2 | 1/2004 |
|---|---|---|
| GB | 2159943 A | 12/1985 |
| JP | 11128197 A | 5/1999 |
| WO | WO 2005045748 A | 5/2005 |
| WO | WO 2005045748 A1 * | 5/2005 |

OTHER PUBLICATIONS

Annex to Form PCT/ISA/206, Communication Relating to the Results of the Partial International Search.

* cited by examiner

*Primary Examiner* — James Kish
*Assistant Examiner* — Michael N Fisher
(74) *Attorney, Agent, or Firm* — Carstens & Cahoon, LLP; Davd W. Carstens

(57) ABSTRACT

A device for determining a person's health that uses a body scanner to obtain a three-dimensional model of a person. The device calculates the volume of at least a first part of the person's body and a second part of a person's body from the three-dimensional model. An indication of the person's health is calculated based on the volume of the first part and volume of the second part of the person's body.

22 Claims, 4 Drawing Sheets

Fig. 3

HEALTH INDICATOR

CROSS-REFERENCE TO RELATED APPLICATIONS

The present application is a 35 USC 371 of PCT Application No. PCT/GB2007/000660, filed Feb. 27, 2007, which claims priority benefits of GB Application No. 0603864.0, filed Feb. 27, 2006 and U.S Provisional Application Ser. No. 60/782,147, filed Mar. 14, 2006.

This invention relates to a health indicator and method of operation of said health indicator. In particular, it relates to a body volume measurement tool for obtaining a measure of whether or not a person has a healthy body mass for their size and/or shape and thus determining the associated health risk. This invention also relates to a method for assisting a person in managing their weight.

A common method, if not the most common method of evaluating whether a person is over or under weight is by use of the Body Mass Index (BMI). The BMI of a person is calculated by dividing their weight (in kilograms) by their height squared (in metres). The BMI gives a general indication of the amount of body fat a person has. The medical terms "overweight" and "obese" are based on BMI values. It is generally accepted that the higher the BMI figure, the more at risk a person is of developing an obesity-related illness. The BMI of a person considered to be healthy is between 18.5 and 24.9. A BMI of less than 18.5 is considered underweight, between 25 and 29.9 is considered overweight, and a BMI of 30 or more is considered obese. It is common for medical practitioners to prescribe drugs to people to assist them in losing weight based, in part, on their BMI.

As stated above, BMI only takes into account the height and weight of a person and does not take account of a person's build, body shape or body composition. The use of ranges of BMI values to define whether a person is healthy, underweight, overweight or obese have, in recent years, been generally accepted in the medical field as being a relatively crude measure of an individual person's health and body shape. For example, people having certain distinctive body shapes can fall into the incorrect BMI category for their actual health and therefore may or may not be receiving the correct intervention or clinical treatment when needed. It is therefore advantageous to have an indicator that is more representative of a person's health, particularly if drugs are prescribed or insurance premiums calculated based on this data.

Obesity or being overweight increases the risk of several different kinds of chronic health problems, for example strokes, high blood pressure, high cholesterol, type 2 diabetes, heart disease and certain types of cancer. However, excess weight does not necessarily mean an increased risk for chronic health problems. Instead, experts believe the amount of lean muscle mass and body fat are more important factors in overall health predictions. A higher percentage of body fat is associated with an increased risk for obesity and weight-related chronic medical conditions and where the fat is distributed over the body is a determining factor.

Body composition analysis determines how much of a person's weight is made up of muscle, bone, skin, water, body organs and fat. The most accurate method for measuring body volume to date is underwater weighing, also known as Hydrostatic Weighing. Using this technique, a measure of the amount of body fat and remaining lean body mass can be obtained. This technique requires a water tank and an underwater scale where a patient is first weighed outside the tank and then, with minimal clothing on the body, sits on a seat mounted with a scale. The seat is then placed into the water tank, totally submerging the patient into the water. This allows the underwater weight to be recorded. Lung capacity is also measured to subtract the weight of the air in the lungs while the patient is holding his/her breath underwater. The total body volume of the person can therefore be determined and an estimated body fat percentage derived from the data obtained.

Underwater weighing is highly accurate, but since the technique requires special equipment, it is usually only used at larger hospitals, and thus availability is an issue. A further drawback is that the procedure cannot be used on everyone and children, elderly and sick people may not be able to co-operate or hold their breath long enough to get an accurate estimate of underwater weight.

A known DEXA (Dual Energy X-ray Absorptiometry) technique uses a scanner that passes low-dose X-rays of differing wavelengths through a person to determine bone density and body fat percentage. Other methods for determining body composition include MRI (Magnetic Resonance Imaging) scanning, BodPod, which uses an air displacement technique, and Tanita, which uses impedance analysis.

According to a first aspect of the invention, we provide a health indicator device comprising a body scanner to obtain a three-dimensional model of a person, a body volume calculator for calculating the volume of at least a first part and a second part of a person's body from the three-dimensional model and a health calculating device for calculating an indication of the person's health based on the output from at least the body volume calculator.

This is advantageous as the three-dimensional (3-D) model is used to calculate the indication of a person's health, which takes into account the unique build and body shape of an individual person. An accurate indication of the person's health can be calculated which can be used to accurately diagnose problems, develop weight change programmes or appropriately prescribe medication or drugs as necessary. It also obviates the need to hydrostatically weigh a patient and is therefore quicker, accurate and less intrusive. The device of the invention is easy to use, non-invasive, patient friendly and completely safe by using non-penetrating radiation imaging techniques, while being particularly accurate and provides a reliable indicator that is representative of a person's health. Further, if the health indicator device is used on a person over a period of time, it can be used to identify people who are at risk of becoming overweight or obese by tracking, comparing and analysing their data. It has been found that using the output from the body volume calculator a more accurate indication of a person's health can be obtained. Using the volume of at least first and second parts of the person's body has been found to be accurate as it takes account of body shape and body mass distribution that cannot easily be realised by making spatial measurements such as waist, chest, bust and hip measurements as in prior art methods. This is especially true if the first or second body parts comprise the abdominal region, which has been found to provide a reliable indication of health risk. The abdominal region contains the intestinal area, liver and kidneys and this region is of importance as its relative volume and composition can be used to accurately predict the risk of type 2 diabetes and cardiovascular disease, for example.

The health calculating device may calculate the indication of a person's health based on the ratio between the volume of the first part and the volume of the second part. This is particularly advantageous as the use of volume ratios of different parts of the body gives an accurate indication of a person's health. Thus, by comparing the volume of various body parts the shape of a person can be recognized. This is advantageous, as the indication of health calculated by the above device is accurate and is able to differentiate between people of different health status but with the same BMI calculation, for example. A sportsman such as a swimmer may have a larger than average chest measurement, which in the prior art methods may be considered unhealthy for their weight, for example. However, the present device may be able to appreciate that the swimmer's body shape is not unhealthy due to the volume of other body parts that the chest volume is compared to. Typical ratios may include neck volume to whole body volume, upper torso volume to abdominal volume or abdominal volume to whole body volume or indeed a combination of these ratios.

Preferably, the body volume calculator determines the volume of third, and/or fourth, and/or fifth and/or sixth body parts and the health calculating device calculates ratios between the volumes of these parts to obtain the indication of a person's health. The health calculating device may use further data such as body composition data to obtain the indication of a person's health. The body composition data may include body fat composition, muscle mass, amount of skin, blood, body water, bone and organs. Preferably, the health indicating device provides a prediction of the volume of the stomach using the volume of the abdominal region obtained from the body volume calculator and body composition data. Which body composition data is used may be chosen depending on the particular part of the body measured by the body volume calculator. Preferably, the body composition data is obtained using cadaver study and analysis data. Most preferably, the body composition data comprises pre-determined data that can be used by the health calculating means to estimate the composition of a part of a person's body based on the volume obtained from the body volume calculator. The pre-determined data may be obtained from published surveys of body composition and in particular such studies by body part.

The body composition data, such as cadaver data, preferably includes data of the weight of constituent elements of a body part and the health calculating device includes comparison means to compare the three-dimensional model to the body composition data to estimate the weight of at least the first body part or second body part based on the volume of those parts calculated by the body volume calculator. This is advantageous as the body composition data allows the health indicating device to estimate how much of a given body part, based on its volume, is made up of skin, bone, water, muscle, etc and therefore estimate its weight. This enables the health calculating device to provide an indication of health and estimate the weight change of parts of the body. Therefore, for example, the person can be informed on which parts of the body to focus their efforts to loose further weight.

Preferably, the health indicator device includes feedback means adapted to receive data regarding the person's health at later time and wherein the health calculating device receives data from the feedback means to improve the accuracy of the indication of a person's health.

The health indicator device may include a height calculating device to obtain the person's height. The indication of the person's health may be calculated using at least the volume of the first and second parts and the person's height.

Preferably, the body volume calculator calculates the volume of predetermined parts of the person's body, which are used by the health calculating device to calculate the indication of the person's health. Preferably, the predetermined parts are associated with an importance factor, which is used to give more importance to particular parts of the body in the calculation of the person's health. Thus, the indication of a person's health can take account of body shape and particular areas of the body where excessive fat deposits are known to be symptomatic of medical conditions. For example, medical researchers have suggested that having excessive fat around the abdominal region has a high correlation with heart disease risk. Thus, the volume of the abdomen and in particular the area between the upper and lower waist may be given a higher importance factor than other parts of the body.

Most preferably, the health calculating device calculates the volume of the abdominal region as the first part, the volume of the upper torso as the second part and the volume of the lower torso as a third part. Preferably, the volume of the first part is compared to the volume of the second and third parts and the importance factor determined therefrom. It will be appreciated that other part body volumes may be used. By determining the indication of a person's health in this way a differential anthropometric measure is created that takes account of differing torso shapes and differing whole body shapes.

Preferably the height calculating device uses the three-dimensional model to calculate the height of the person. Preferably, the health calculating device receives a measurement of the length of the person's legs. This may be measured and entered manually, although preferably the measurement is made by the device from the three-dimensional model. Preferably, the length of the person's legs is used by the health calculating device to determine the indication of a person's health. This is advantageous as research has shown that people with short legs in relation to the rest of their body are prone to insulin resistance.

Preferably the health indicator device includes a blood pressure measurer to obtain the person's blood pressure. This may be measured during the scanning of the person's body or afterwards. The health indicator may also include a cholesterol measurement device. Preferably, the device includes means to obtain the body composition of the person or a particular part of the body of that person. Preferably, the device includes means to measure the person's heart rate or heart rate variability. Preferably the body volume calculator comprises software that manipulates data output from the body scanner and may obtain additional data. Preferably, the additional data includes cholesterol level, blood pressure, lipids profile and glucose or weight. Preferably the body volume calculator manipulates the data output from the body scanner using triple integration.

The body scanner may be of known type and preferably is a scanner of white light type. This is advantageous as it does not subject the person to a dose of radiation like certain known scanning techniques. In summary, such a scanner makes many measurements (typically 100 to 130 million) known as data points of several million positions on the surface of a person's body. These data points can then be appropriately joined or associated with neighbouring points to form a three-dimensional image of a person. An appropriate body scanner is an $NX_{12}$ or $NX_{16}$ scanner manufactured by $(TC)^2$ of 211 Gregson Drive, Cary, N.C. 27511 USA, for example. It will be appreciated that other scanners capable of taking the appropriate measurements to generate the model may also be used.

Preferably the indication of a person's health is scaled such that it corresponds to the known BMI scale. This is advantageous as it provides a value that is an accurate representation of a person's health that is readily recognised as it modified to correspond to a widely known and long established BMI scale. Preferably the indication is scaled by a constant. However, it may be scaled by a function.

Preferably the health indicator device stores the 3-D model and the indication of a person's health. Preferably the health indicator device determines whether the person being scanned has been scanned previously and, if so, shows at least a comparison between the present 3-D model and the previous 3-D model. It may also show comparison information with average or aggregated scans of people with similar measurements or the national average or international average. The device may also show a comparison between the previous indication of a person's health and the present indication of a person's health.

Preferably the health indicator device is used to collect statistics, which are stored in a database. Preferably, the database can be accessed from a secure web server.

According to a second aspect of the invention, a method for calculating the health of a person comprising the steps of;
  scanning the person's body using a body scanner;
  generating a three-dimensional model of the person's body;
  calculating the volume of a first part of the person's body from the three-dimensional model;
  calculating the volume of a second part of the person's body from the three-dimensional model; and
  calculating an indication of the health of the person from at least the calculated volume of the first and second parts of the person's body.

The indication of health is obtained quickly, easily and accurately by the above method. As a body scanner is used the data collected is a true and undistorted representation of a person's size and shape. The calculation of a person's volume or, in particular, the volume of predetermined body parts using a body scanner gives an accurate representation of a person's shape without the need to submerge them in water, for example. Further, the present method allows the volume of parts of the body to be determined and, using predetermined data or further measurement, an estimate of the body composition per body section can be obtained. The indication of health obtained provides a useful anthropometric measure that is an accurate assessment of a person's health and can be used as an alternative to BMI and other manual based anthropometric measurement techniques.

Preferably, the indication of the person's health is calculated by the ratio between the first volume and the second volume. As discussed in relation to the first aspect of the invention, the volume of various first and second body parts may be chosen. However, the first body part preferably comprises the abdominal area and the second body part preferably comprises the upper torso.

Preferably, the volume of further predetermined parts of the person's body are calculated and used in the calculation of the indication of the person's health. The person's weight, height and/or leg length may be used in the calculation of the indication of the person's health.

Preferably, the method includes obtaining body composition data based on the volume of the first or second parts and using the body composition data in the indication of a person's health.

Preferably the method includes obtaining a blood pressure measurement of the person. This may be measured during the scanning of the person's body or afterwards. The method may also include measuring the cholesterol level of a person. The blood pressure and/or cholesterol measurement may be used in the calculating of the health of a person. A blood sample may also be taken.

According to a third aspect of the invention, we provide a method of weight management comprising the steps of;
  (a) scanning a person's body using a body scanner;
  (b) generating a three-dimensional model of the person's body;
  (c) measuring at least the person's weight;
  (d) generating a data record including the three dimensional model and at least the person's weight; and
  (e) repeating steps (a) through (d) at predetermined time intervals and generating a further data record showing any changes in the three dimensional model and/or at least the person's weight.

This is advantageous as the person undergoing weight management has a representation of how their body shape is changing. Thus, by having the graphical representation of their body shape as well as the numerical data, it gives the person a more informative insight into what has been achieved and what still needs to be achieved. This method is particularly applicable in a healthcare setting. Further, simply seeing the 3-D representation may encourage and motivate the person into admitting that a change in weight is necessary and act as a psychological tool for healthcare purposes. This is particularly useful for people with eating disorders such as Anorexia or elderly patients who suffer from malnutrition as the perception of their own body shape differs from reality. A common symptom of Anorexia is denial that they are painfully thin. Indeed many anorexics truly believe they are overweight. By showing them an image of their body from the 3-D model, it may have the required psychological impact to help them accept the reality that they are severely underweight and have a medical condition. Further, use of a scanner is less invasive than having another person make numerous "hands-on" measurements and there is no intervention. Still further, manually measuring someone can lead to inaccuracies due to how tight the measuring tape is held, which can, for example, compress soft areas leading to an inaccurate reduced measurement. This problem is common as often, the measuring tape bridges the small of the back between body mass either side of the spine. Thus, the person is more relaxed due to the absence of physical contact and the data collected is more accurate and also very detailed.

The further data sheet preferably shows the three-dimensional models of the body taken at each predetermined time to visually show any changes. Most preferably the models of the body are overlaid on one another or they may be positioned side by side. The further data sheet may include additional information, and/or changes in said additional information, such as neck, chest, waist and hip measurements, blood pressure, cholesterol level, blood analysis, heart rate and variability. The data sheet or further data sheet may be such that it can be sent to the patient by e-mail or by SMS or MMS message to a mobile phone. The sending of data in this way may be effected via a website such as www.bodyvolume.mobi.

The predetermined time intervals may be between 1 and 52 weeks and are preferably between 10 and 15 weeks. Most preferably the time interval is 13 weeks, although it will be appreciated that time intervals between scans may vary according to individual patient needs or healthcare diagnosis by healthcare professionals.

Preferably, the method of weight management defined employs the use of the health indicator device of the first aspect of the invention.

According to a fourth aspect of the invention, a method for assisting a person to change weight comprising the steps of:
  (a) arranging for payment of a number of sessions;
    said session at least comprising scanning said person in a body scanner and generating a three-dimensional model of said person;
  (b) scheduling a further session;

(c) performing said further session and generating a data sheet showing at least said three-dimensional model from the present session and any changes from the previous session;

(d) repeating steps (b) and (c) until the number of sessions completed is equal to the number of sessions payment has been arranged for.

Preferably the further session is scheduled between 4 and 13 weeks after the present session or at a suitable time as determined by a clinician. Preferably payment is arranged to be made prior to the first session being performed by debit card, credit card, for example. Payment may be arranged or made remotely, for example via the Internet by way of email or via a web site.

Preferably the session includes the steps defined in accordance with the second aspect of the invention or using the device of the first aspect of the invention.

According to a fifth aspect of the invention we provide a database means adapted to receive at least one record, the record comprising an identification reference associated with a person and at least information obtained by scanning the person using a body scanner, wherein the database means includes access means to allow access to the information stored in the database means.

Preferably the identification reference comprises the date of birth or name of the person that is scanned. However it may comprise other identifying information such as a national insurance number, identity card number or social security number. Alternatively, it may be a serial number that is assigned to the information obtained from the scanner. Most preferably, the identification reference is derived from the gender, date of birth, date and time of the scan, ethnicity and the location of where the scan was performed. Accordingly the database means stores anonymous information and therefore the identifying information of the person who was scanned is associated with the identification reference and is stored elsewhere. Preferably, the database is available via a secure server to users with appropriate secure authentication and permission.

Preferably the information obtained by scanning the person comprises a three-dimensional model of the person's body. Preferably the information includes the volume of a first part and a second part of the person's body calculated from the three-dimensional model of the person's body. Preferably the information includes body composition data derived from the body volume measurements of at least the first and second parts of the person's body. Preferably the information includes an indication of the person's health derived from the volume, calculated from the three-dimensional model, of at least the first and second predetermined parts of the person's body. Preferably, the predetermined parts are associated with an importance factor, which is used to give more importance to particular parts of the body in the calculation of the person's health. The importance factor may comprise a multiplier or alternatively it may be a function. Preferably the calculation of a person's health comprises an algorithm that uses a plurality of ratios of the volume of predetermined parts of the person's body. Preferably the importance factor is determined from any combination of the gender, age and ethnicity of the person.

Preferably, the database means is located on a computer server. Preferably the access means is adapted to allow access to the information over the Internet. Preferably the access means allows access to the information over a secure channel, such as SSL (Secure Socket Layer). Preferably, the access means requires registration details or payment to allow access to the information. The use of registration details allow only the appropriate people to access the information, such as the person to whom the information relates, their medical practitioners, health professional or other person they specify as being able to access the data.

Preferably the database means is adapted to receive a plurality of entries for each identification reference and the date on which the information from the body scanner is obtained.

According to a sixth aspect of the invention, we provide a health indicator device comprising a body scanner to obtain a three-dimensional model of a person, a body volume calculator for calculating the volume of at least a part of the person's body from the three-dimensional model, a height calculating device to obtain the person's height and a health calculating device for calculating an indication of the person's health based on the output from at least the body volume calculator and the height calculating device.

According to a seventh aspect of the invention, a method for calculating the health of a person comprising the steps of;
  scanning the person's body using a body scanner;
  generating a three-dimensional model of the person's body;
  calculating the volume of at least a part of the person's body from the three-dimensional model;
  measuring the height of the person's body; and
  calculating an indication of the health of the person from at least the calculated volume and height of the person's body.

According to an eighth aspect of the invention, we provide a method of weight management comprising the steps of;
  (a) scanning a person's body using a body scanner;
  (b) generating a three-dimensional model of the person's body;
  (c) measuring at least the person's height and weight;
  (d) generating a data sheet including the three dimensional model and at least the person's weight; and
  (e) repeating steps (a) through (d) at predetermined time intervals and generating a further data sheet showing any changes in the three dimensional model and/or at least the person's weight.

According to a ninth aspect of the invention there is provided a machine readable medium containing instructions to allow any of the above methods to be provided.

According to a tenth aspect of the invention there is provided a machine readable medium containing instructions to cause any of the above apparatus to function.

The machine readable medium according to any of the above aspects of the invention may comprise any of the following: a floppy disk, a CDROM/RAM, a DVD ROM/RAM (including -R/-RW and +R/+RW), a Blu ray disc, an HD DVD, a memory (including a Memory Stick, SD card, Flash memory card or the like), a hard drive, any form of magneto optical storage, a transmitted signal (including an Internet download, an FTP transfer or the like), a wire.

According to an eleventh aspect of the invention, we provide a method of calculating the weight of parts of a person's body comprising the steps of;
  scanning a person in a body scanner;
  generating a three-dimensional model of the person's body;
  splitting the three-dimensional model into at least one part;
  calculating the volume of the at least one part from the three-dimensional model;
  using the volume of the or each body part and cadaver data to estimate the composition of the or each body part.

This is advantageous as the method allows detailed analysis of the composition of body parts without the need for scanning techniques that use body-penetrating radiation.

Thus, the above method allows the amount of organs, blood, water or tissue, for example, to be accurately estimated from the volume of the body part and the cadaver data. A white light body scanner may be used, which provides a cost effective method of obtaining accurate composition analysis of a person's body by body part. It will be appreciated that other body scanners may be employed such as MRI, CT or BodPod, for example.

The method may include the step of using the volume of the or each body part and the cadaver data to estimate the weight of each component of that body part. The components of a body part such as an arm may include the weight of the skin, bone, muscle mass, body fat or adipose tissue, blood and water. For the upper torso the components may include the weight of the Lungs, Heart, Spleen and all the skin, bone, muscle mass, body fat or adipose tissue, blood and water. For the lower torso the components may include the reproductive organs, Bladder and all the skin, bone, muscle mass, body fat or adipose tissue, blood and water. For the abdominal area the components may include the Liver, Kidneys, Large Intestine, Small Intestine, Stomach and all the skin, bone, muscle mass, body fat or adipose tissue, blood and water. It will be appreciated that other body parts will be analysed according to their relevant components.

Although the components differ depending on which part of the body is analysed, preferably the weight of at least the amount of blood, bone, water, tissue and fat is determined. In this context fat is assumed to be the amount of lipids extractable from adipose tissue.

There now follows by way of example only a detailed description of embodiments of the present invention with reference to the accompanying drawings in which;

FIG. 3 shows a datasheet that may be generated using the weight management method.

The embodiments described herein relate to a health indicator device that can be used in the assessment of a person's or patient's health. The device disclosed can also be used as a weight management tool as also described below. The health indicator device will typically be situated in Hospitals, Doctor's Surgeries, Health Centres, Clinical Trial Facilities, Fitness Clubs, Gymnasiums and Private Health Care providers and will be used by medical professionals, Dieticians and Nutritionists to monitor weight loss or weight gain in patients. The device and method may even be applied to slimming clubs or to assessment of health insurance premiums, as an alternative to simply being weighed and the person's BMI being calculated manually.

Figure 1:
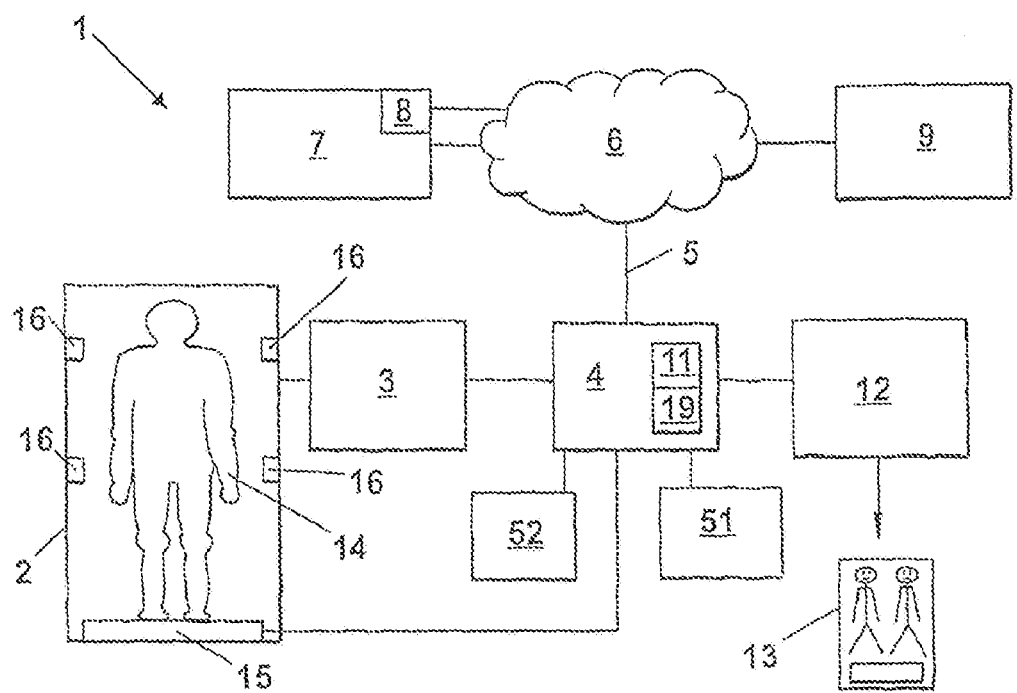
FIG. 1 shows a diagrammatic representation of the health indicator device.

In FIG. 1, a health indicator device 1 is shown comprising a body scanner 2, data collection means 3 and manipulation means 4. The manipulation means 4 has a connection 5 to the Internet 6 so that it can communicate with database means 7. It will be appreciated that the connection need not be via the Internet 6 and may be over a Local Area Network, a direct connection or over a telephone line depending upon the location of the manipulation means 4 and the database means 7. The database means 7 also has access means 8 to enable it to be accessed remotely by health professionals such as general practitioner or GP 9. In this embodiment, the GP can access the database means 7 via the access means 8 over the Internet via a web-based interface.

The connection 5, 6 between the manipulation means 4 and the database means 7 comprises a secure file transfer protocol connection, although any appropriate connection, secure or otherwise, could be used. The connection between the GP 9 and the database means 7 is also a secure connection, using known secure Internet transfer methods such as SSL.

The body scanner 2 comprises a $NX_{16}$ white light scanner manufactured by $TC^2$. The scanner uses a plurality of white light sources to illuminate the person's body such that sensors can obtain measurements of the size and shape of the person for the generation of a three-dimensional model.

The data collection means 3 comprises software loaded onto a computer that is connected to the scanner 2. The manipulation means 4 also comprises software loaded on to the same computer, wherein the manipulation software receives its input from the output of the scanner software 3. The manipulation software 4 includes a body volume calculator 11 and a health calculating device 19 both embodied as software.

The manipulation means 4 passes the data from the data collection means 3 to the body volume calculator 11 with any additional information as appropriate. For example, the manipulation means may specify which body parts the volume calculator 11 should calculate the volume of. The output from the body volume calculator 11 is passes to the health calculating device 19. The device 19 calculates a ratio between the first volume, corresponding to the first body part output by the volume calculator, and the second volume corresponding to the second body part output by the volume calculator. The manipulation means 4 also receives input from body composition database means 51. The database means 51 contains information from medical surveys, for example, on the composition of people of different sizes, shapes, gender, ages and ethnicity. Thus, by comparing the information entered into the manipulations means 4 about the person being scanned and the measurements made from the three-dimensional model, the manipulation means 4 can extract the typical body composition for that person from the database means 51. This information is used by the health calculating device 19, in combination with the ratio between the first and second volumes to generate the indication of a person's health. The indication of a person's health obtained can be used by the GP to assess the person's health and the health risks they could potentially by prone to. The GP can then recommend preventative measures, changes to diet, exercise or medication to improve the health of the person scanned.

The manipulation means 4 also receives input from a feedback means 52. The feedback means receives information entered by a GP, for example, about any health problems that have developed in the scanned person. Such information can be used by the manipulation means can be used to validate or improve the indication of a person's health initially calculated by the health calculating device 19. For example, if the indication of a person's health indicated that the person had a high risk of heart disease and subsequently that person developed heart disease, this information can be received by the feedback means 52. The health calculating device 19 then alter an importance factor associated with the body volumes it used to calculate the indication of a person's health, so that subsequent calculations of people with a similar size, shape or composition yield an indication of health that emphasises the health risk to a GP. The feedback means 52 therefore provides the device 1 with a means to validate and iteratively improve the accuracy of the results the health indicator device 19 produces.

The connection 5 may also be used to update the manipulation software 4 from a computer server (not shown) also connected to the Internet.

The manipulation means 4 is also connected to an output means 12, which comprises a printer. The printer 12 is able to print a datasheet 13, 50 showing at least the output from the manipulation means 4.

Figure 2:
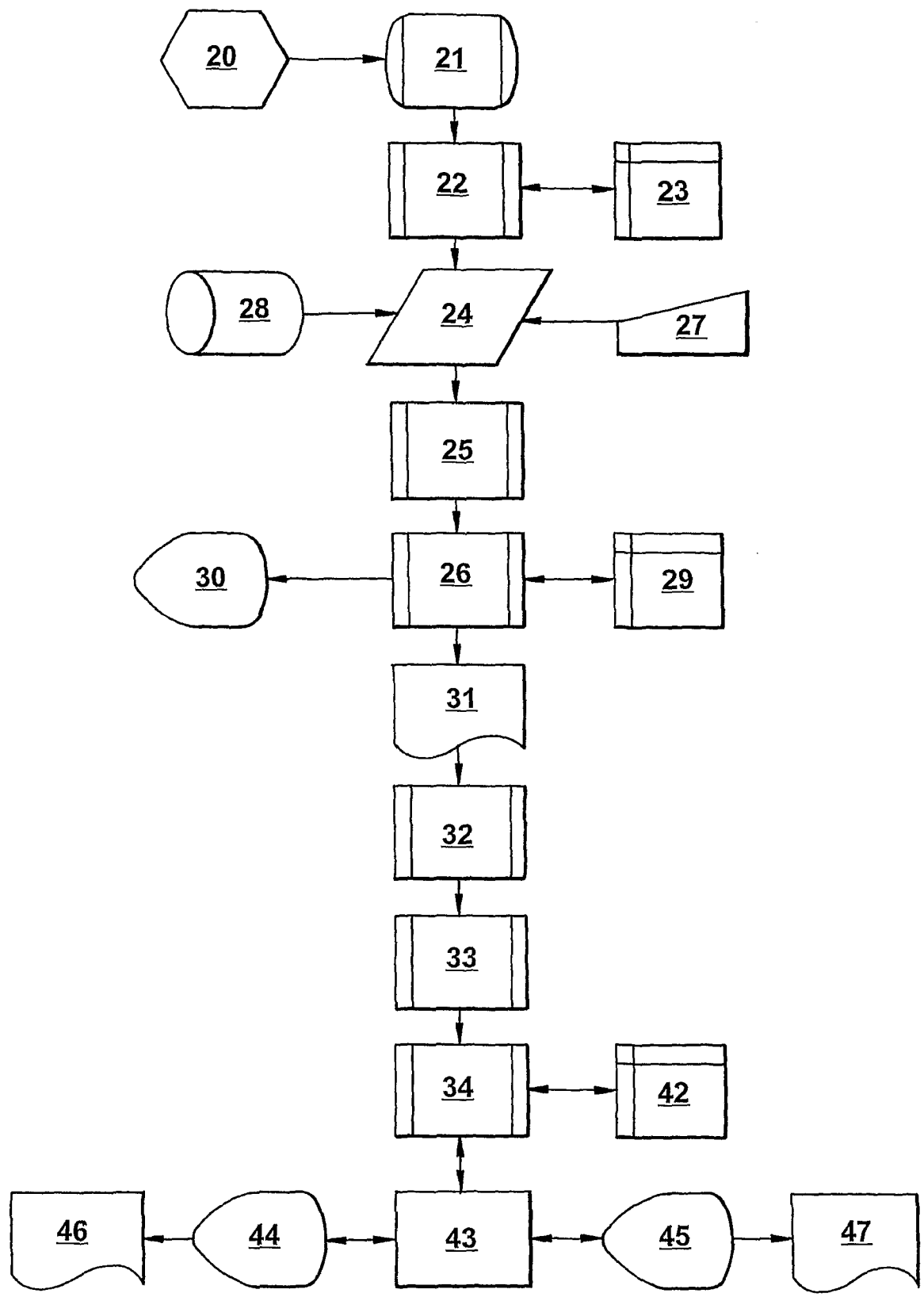
FIG. 2 shows a flow chart of the operation the health indicator device and the database means.

FIG. 2 shows a flow chart of the scanning method. In use, an operator would oversee the scanning process. The operator would brief a person 14 (shown in FIG. 1) to be scanned on the scanning process including what posture to adopt and how to initiate the scanning process. The person 14 would undress to underwear in a changing booth adjacent the scanner 2. These steps are represented by numeral 20. The person 14 is scanned at 21, which involves entering the scanner 2 and adopting the predetermined position and initiating the scanning process.

The scanners used by embodiments of the present invention are known and will not be described in detail. However, in summary, a plurality of white light sources 16 emit light in a specific pattern which is then incident on the person's body 14. A plurality of cameras (not shown) are used to make measurements based on the pattern of light reflected from the person's body. The resultant raw data comprises a "3-D cloud" of data points that is processed by the data collection means 3 at step 22 to generate a "wire-frame" three-dimensional model of the person 14. The raw or model data is stored 23 in storage means (not shown). The stored data can be recalled from the storage means as required. The storage means may comprise memory, a hard disk and optical media or may be a remote device connected to the data collection mean 3 by communication means. The data collection means 3 may also make simple calculations on the model data such as the height of the person 14. Therefore, the model data and the calculations are received by the manipulation software 4.

The data from the data collection means 3 is output to the manipulation software 4. Steps 24 and 25 represent part of the method performed by the manipulation software 4. The manipulation software 4 is adapted to receive additional information at step 24 about the person 14 being scanned. This additional information is received automatically via other external devices 28 such as weighing scales 15, cholesterol meters (not shown) and/or blood pressure measurers (not shown). Further additional information is also input manually 27 from records or by physically making measurements. The information received automatically may be via a dedicated device interface or a serial connection, for example. It will be appreciated that any appropriate means for receiving the information may be employed.

Step 25 represents at least the actions performed by the body volume calculator 11 and the health-calculating device 19. The body volume calculator modifies the 3-D model data and applies a triple integration to calculate the volume. It will be appreciated that any appropriate method may be used by the volume calculator 11 to calculate the volume of the first body part and the second body parts. The first and second volumes calculated from the model therefore correspond to the volume of the person 14 or part volume thereof.

At step 25 the body volume calculator 11 uses the model data output by the data collection means 3 to identify and calculate the volume of parts of the model that correspond to predetermined parts of the person's body 14. The volume calculator 11 calculates at least the volume of a first part, such as the mid-section around the stomach, and a second part, which may comprise the volume of the person's whole body. The parts chosen may vary depending upon the person's weight problem or medical condition or the health risk to be predicted. The volumes of the various parts of the model calculated by the body volume calculator 11 are passed to the health-calculating device 19. The volume of these predetermined parts, such as the abdominal region, backside, or hips for example, are then associated with an importance factor. Similarly, the importance factor associated with each part of the body will vary depending upon the person's weight problem or medical condition. The importance factor may be used to apply a bias to the volumes calculated for certain parts of the body. Thus, the indication of a person's health can take account of the impact on the health that different body fat and adipose tissue distributions will have. The use of importance factors could also be used to take account of the composition of different parts of the body due to differing bone, tissue or organ masses if the weight or body density of a person is used in the calculation of a person's health. However, in this embodiment the data collection means 3 is adapted to receive data from the body composition database 51. The data from the body composition database allows the health calculating device 19 to estimate the body composition of the person being scanned. It will be appreciated that the importance factor may comprise a function, the coefficients of which may take account of sex, gender, ethnicity, age, other biometric data and the information from the feedback means 52.

The health-calculating device 19 then calculates an indication of the person's 14 health using the ratio between the first and second volumes of the parts of the body and their associated importance factors. It will be appreciated that the manipulation software 4 and volume calculator 11 can be programmed to calculate the appropriate volume or volumes depending on the person's 14 condition or the application of the device 1. For example, for medical purposes, the model of the body 14 may be separated into many parts, each being associated with an importance factor to obtain an accurate and representative indication of a person's health. The importance factor also allows for the natural differences in body shape caused by gender, age and ethnicity to be taken account of. Thus, the device may use the ratio of the volume of the persons abdominal region to the whole body volume and scale it appropriately by the importance factor. Alternatively, when the device 1 is used in a gymnasium, the indication of a person's health may be calculated using the volume of the person's 14 whole body.

Once the manipulation software 4 has performed its manipulation 25 of the data output from the data collection software 3, a record is created of the person's scan and the statistics calculated by the manipulation software 4. If the person 14 has been scanned previously, the model data and other statistics are appended to the previously created record at step 26. The record is also stored 29 and displayed to the person and/or operator on a display means (not shown) at step 30.

Figure 3:
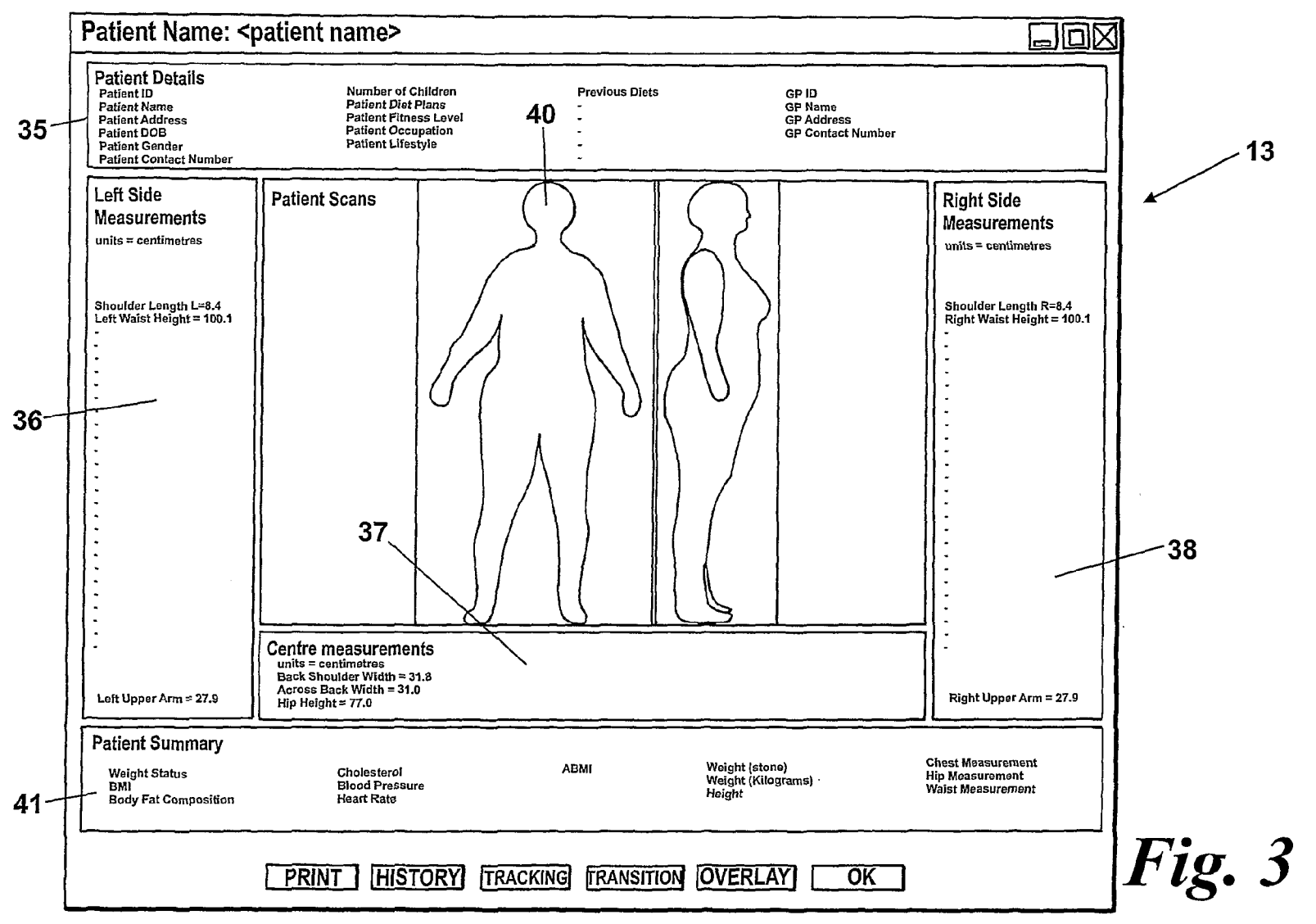

A datasheet 13 (or further datasheet if data of a previous scan is included) is printed at step 31 by the output means 12. Two exemplary views of the output from the display means from which the datasheet is printed is shown in FIGS. 3 and 4. The sheet includes personal details 35 of the scanned person 14 and measurements 36, 37, 38 made from the three-dimensional model of the person's body. The personal details may include an identification reference assigned to the person, their name, address, date of birth, occupation, lifestyle, medication being taken, allergies and details of their general practitioner, for example. The measurements 36, 37, 38 may include arm and leg lengths and widths and waist, hips, chest, bust, underbust, bicep, thigh and neck measurements, for example. The datasheet 13 also includes a graphical representation 40 of the three-dimensional model shown in front view and in side view. The provision of the graphical representation 40 has a psychological impact on many patients as they are presented with an accurate image of their body that is more abstract than a photograph or reflection in a mirror. Thus, people are more likely to readily accept the graphical representation 40 as an accurate representation than deny to themselves that they do not have a weight problem, for example. This is particularly useful for people who have the potential to become obese with it's related health problems or those suffering from eating disorders, such as anorexia, where the person believes, when looking at their body in the flesh, that they are overweight. Finally, a summary 41 of the statistics and the indication of the person's health is provided calculated from the volumes of the first and second parts of the body.

Figures 4A, 4B:
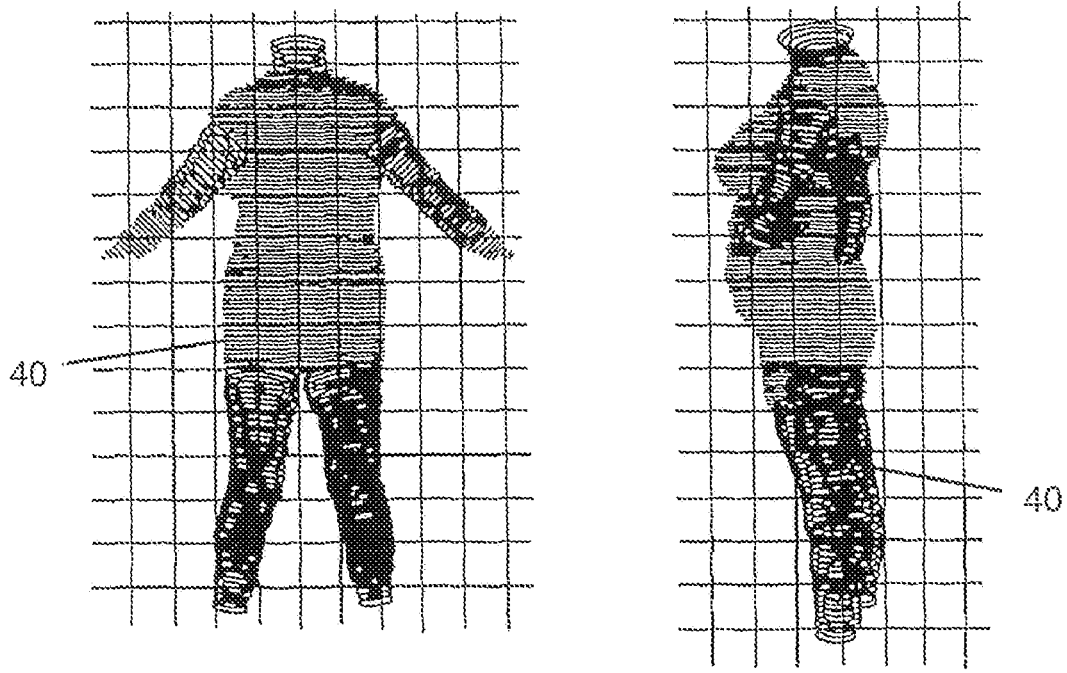
FIGS. 4A and B shows a portion of a further datasheet.

A further datasheet may be substantially similar to that shown in FIG. 3, but will show any changes in the measurements and/or 3-D model. Thus, the further datasheet is a composite data sheet showing information from two or more data sheets. FIGS. 4A and B show how the changes in the model may be represented in the composite datasheet. FIG. 4A shows the 3-D model after the person has been scanned at a first time. FIG. 4B shows two 3-D model sections overlaid to show the change in body size and body shape. The composite data sheet may also include graphs showing the change in size over time of various body parts.

Referring back to FIG. 2, a file is created 32 from the patient record that includes the three-dimensional model and the values calculated by the manipulation software 4. The file does not (although it may) contain the personal details of the scanned person 14, but only the identification reference. The file may be compressed. At step 33, it is sent to the database means 7. The database means 7 interprets the data and determines, from cross-referencing the identification reference with the contents of the database, whether the record is new or in addition to data already stored. Accordingly, the database means creates a new record or appends then data contained in the file to a previously created record and stores 42 the record. The information store of the database means is secure to prevent unauthorised access to the data contained therein.

The access means 8 comprises a secure web-based interface 43. The interface 43 allows secure access to the database means 7 by using registration details such as a username and password that is transmitted to the database means over a SSL connection. Thus, the access means transmits the appropriate record to the GP as represented by step 44 and/or to the person 14 represented by step 45. The record can then be printed 46, 47 as required.

Figure 5:
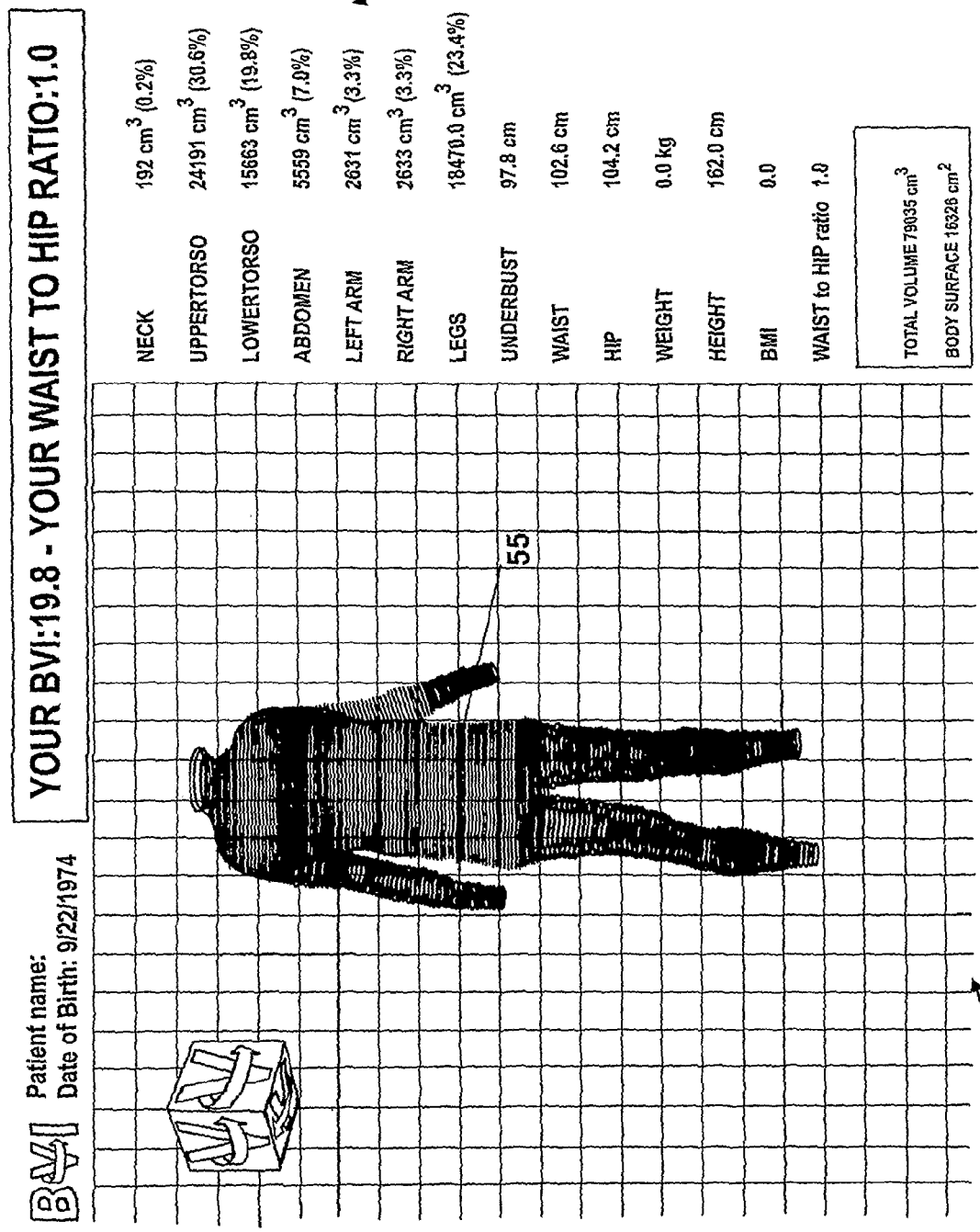
FIG. 5 shows a second embodiment of the datasheet.

FIG. 5 shows a second datasheet 50 printed by printer 12. This datasheet shows a representation of the three-dimensional model 55 generated by the device 1. It also includes a plurality of measurements 56, some of which are calculated by the body volume calculator. In particular, the volume of the neck, upper torso, lower torso, abdomen, left arm, right arm, legs and total body is shown as calculated from the three-dimensional model obtained by scanning the person. The indication of a person's health is given as a figure labelled BVI, which may be calculated using the ratios between the above-mentioned volumes.

The invention claimed is:

1. A health indicator device comprising:
    body scanner;
    body volume calculator:
    body database; and
    health calculating device
    wherein
    said body scanner is configured to obtain a three-dimensional model of a person;
    said body volume calculator is configured to calculate from said three-dimensional model first volume comprising a first body part of said person and a second volume comprising a second body part of said person;
    said health calculating device is configured to calculate an indication of the health of said person using the body composition of said person by retrieving composition data from said body database and incorporating said composition data into said first volume and said second volume and calculating said indication using a ratio of said incorporated first volume to said incorporated second volume.

2. A health indicator device according to claim 1, in which the body volume calculator is arranged to calculate the volume of further predetermined parts of the person's body, which are used by the health calculating device to calculate the indication of the person's health.

3. A health indicator device according to claim 2, in which the device is arranged to associate the first, second and any further predetermined parts with an importance factor, which is used to give more importance to particular parts of the body in the calculation of the person's health.

4. A health indicator device according to claim 3, in which the device is arranged to give the volume of the abdomen a higher importance factor than other parts of the body.

5. A. health indicator device according to claim 3, in which the device is arranged to give the volume of the upper and lower waist a higher importance factor than other parts of the body.

6. A health indicator device according to claim 1, in which the health indicator device further comprises a blood pressure measurer arranged to obtain the person's blood pressure.

7. A health indicator device according to claim 1, in which the health indicator device further comprises a cholesterol measurer.

8. A health indicator device according to claim 1, in which the body volume calculator comprises software that manipulates data output from the body scanner.

9. A health indicator device according to claim 1, in which the body volume calculator is arranged to manipulate the data output from the body scanner using triple integration.

10. A health indicator device according to claim 1, which is arranged to use the length of the person's legs, calculated from the three-dimensional model by the health calculating device to determine the indication of a person's health.

11. A health indicator device according to claim 1, in which a height calculating device is arranged to use the three-dimensional model to calculate the height of the person and the height is used in combination with the length of the person's legs by the health calculating device.

12. A health indicator device according to claim 1, which is arranged to scale the indication of a person's health such that it corresponds to a known BMI scale.

13. A health indicator device accord claim 12, in which the indication is scaled by a constant.

14. A health indicator device according to claim 12, in which the indication is scaled by a function.

15. A health indicator d vice according to claim 1, in which the health indicator device is arranged to store the 3-D model and the indication of a person's health.

16. A health indicator device according to claim 1, in which the health indicator device is arranged to determine whether the person being scanned has been scanned previously and, if so, is arranged to show at least a comparison between the present 3-D model and the previous 3-D model.

17. A health indicator device according to claim 1, in which the device is adapted to show comparison information with average or aggregated scans of people with similar measurements.

18. A health indicator device according to claim 1, in which the device is arranged to show a comparison between any previous indication of a person's health and a present indication of a person's health.

19. A health indicator device according to claim 1, in which the health indicator device is used to collect statistics, which are stored in a database.

20. A method for calculating the heath of a person comprising the steps of:
scanning the body of person using a body scanner;
generating a three-dimensional model of said body;
calculating from said three-dimensional model a first volume comprising a first body part of said person;
calculating from said three-dimensional model a second volume comprising a second body part of said person; and
calculating a health indication of said person using the body composition of said person by retrieving composition data from a body database and incorporating said composition data into said first volume and said second volume and calculating a ratio of said incorporated first volume to said incorporated second volume.

21. A non-transitory machine readable medium containing instructions which when read by a machine causes that machine to perform as the health indicator device of claim 1.

22. A non-transitory readable medium containing instructions which when read by a machine causes that machine to perform the method of claim 20.

* * * * *